(12) United States Patent
Deem et al.

(10) Patent No.: US 8,679,171 B2
(45) Date of Patent: Mar. 25, 2014

(54) DEVICES AND METHODS FOR TREATMENT OF ABDOMINAL AORTIC ANEURYSM

(75) Inventors: Mark Deem, Mountain View, CA (US); Hanson S. Gifford, III, Woodside, CA (US); Bernard Andreas, Redwood City, CA (US); Sunmi Chew, San Jose, CA (US); Ron French, Santa Clara, CA (US); Doug Sutton, Pacifica, CA (US)

(73) Assignee: The Foundry, LLC, Menlo Park, CA (US)

( * ) Notice: Subject to any disclaimer, the term of this patent is extended or adjusted under 35 U.S.C. 154(b) by 1722 days.

(21) Appl. No.: 10/791,469

(22) Filed: Mar. 1, 2004

(65) Prior Publication Data

US 2004/0193245 A1 Sep. 30, 2004

Related U.S. Application Data

(60) Provisional application No. 60/458,286, filed on Mar. 26, 2003.

(51) Int. Cl.
*A61F 2/06* (2013.01)

(52) U.S. Cl.
USPC .......................................................... 623/1.11

(58) Field of Classification Search
USPC ............. 623/1.35, 1.11–1.15; 606/1.12, 1.13, 606/1.15
See application file for complete search history.

(56) References Cited

U.S. PATENT DOCUMENTS

| | | | |
|---|---|---|---|
| 3,608,088 A | | 9/1971 | Dorman et al. |
| 4,135,253 A | | 1/1979 | Reich et al. |
| 5,316,023 A | * | 5/1994 | Palmaz et al. ................. 128/898 |
| 5,360,443 A | * | 11/1994 | Barone et al. ................. 623/1.13 |
| 5,449,342 A | | 9/1995 | Hirose et al. |
| 5,507,769 A | * | 4/1996 | Marin et al. ................. 606/198 |
| 5,571,173 A | * | 11/1996 | Parodi ........................... 623/1.13 |
| 5,665,117 A | * | 9/1997 | Rhodes .......................... 623/1.1 |
| 5,683,453 A | * | 11/1997 | Palmaz ......................... 623/1.13 |
| 5,722,930 A | | 3/1998 | Larson, Jr. et al. |
| 5,762,599 A | | 6/1998 | Sohn |
| 5,843,168 A | * | 12/1998 | Dang ............................ 623/1.15 |

(Continued)

FOREIGN PATENT DOCUMENTS

| | | |
|---|---|---|
| WO | WO 97/12562 A | 4/1997 |
| WO | WO 01/30270 A | 5/2001 |
| WO | WO 01/39700 A | 6/2001 |
| WO | WO 01/30270 A3 | 12/2001 |

OTHER PUBLICATIONS

Supplementary European Search Report of EP Application No. 04714629.5, dated Feb. 25, 2009, 4 pages total.

(Continued)

*Primary Examiner* — Gregory Anderson
(74) *Attorney, Agent, or Firm* — Wilson Sonsini Goodrich & Rosati

(57) ABSTRACT

Devices and methods for treating aneurysms, such as abdominal aortic aneurysms ("AAA") generally include one or more stent-graft devices. Some embodiments include self-expanding and/or balloon-expandable stent components and one or more graft components coupled with the stent components. Using various combinations of self-expanding stent members, balloon-expandable stent members, graft members, and/or anchoring members enhances the anchoring abilities of a stent-graft device to prevent leakage around it, and may further allow the device to be adjusted after placement at a site for treatment. Some embodiments further include a skirt graft member for further prevention of leakage and/or device slippage.

47 Claims, 12 Drawing Sheets

(56) References Cited

U.S. PATENT DOCUMENTS

| | | | |
|---|---|---|---|
| 5,843,176 A * | 12/1998 | Weier | 623/1.2 |
| 5,855,598 A * | 1/1999 | Pinchuk | 623/1.13 |
| 5,860,998 A | 1/1999 | Robinson et al. | |
| 5,944,750 A * | 8/1999 | Tanner et al. | 623/1.23 |
| 6,162,246 A * | 12/2000 | Barone | 623/1.35 |
| 6,168,621 B1 * | 1/2001 | Vrba | 623/1.2 |
| 6,409,750 B1 * | 6/2002 | Hyodoh et al. | 623/1.1 |
| 6,530,876 B1 | 3/2003 | Spence | |
| 6,887,268 B2 * | 5/2005 | Butaric et al. | 623/1.35 |
| 6,945,994 B2 * | 9/2005 | Austin et al. | 623/1.16 |
| 7,044,962 B2 * | 5/2006 | Elliott | 623/1.13 |
| 7,160,318 B2 * | 1/2007 | Greenberg et al. | 623/1.13 |
| 7,314,483 B2 * | 1/2008 | Landau et al. | 623/1.35 |
| 2001/0039369 A1 | 11/2001 | Terentiev | |
| 2002/0026214 A1 | 2/2002 | Tanner et al. | |
| 2002/0177891 A1 | 11/2002 | Parodi | |
| 2003/0130724 A1 | 7/2003 | DePalma et al. | |
| 2003/0236567 A1 * | 12/2003 | Elliot | 623/1.13 |
| 2004/0193254 A1 * | 9/2004 | Greenberg et al. | 623/1.35 |

OTHER PUBLICATIONS

International search report dated Sep. 14, 2004 for PCT Application No. US04/005695.

* cited by examiner

DEVICES AND METHODS FOR TREATMENT OF ABDOMINAL AORTIC ANEURYSM

CROSS-REFERENCES TO RELATED APPLICATIONS

This application claims the benefit under 35 USC 119(e) to provisional Patent Application Ser. No. 60/458,286, filed Mar. 26, 2003, the full disclosure of which is incorporated herein by reference.

BACKGROUND OF THE INVENTION

The present invention relates to devices and methods for treating aneurysms. More particularly, the invention relates to devices and methods for treating abdominal aortic aneurysms including stents with self-expanding and balloon-expandable features.

An aneurysm is a sac formed by localized dilatation of the wall of an artery, a vein, or the heart. Common areas where aneurysms occur and cause potential medical conditions include the coronary arteries, the carotid arteries, various cerebral arteries, and the abdominal aorta. When a local dilatation of a vessel occurs, irregular blood flow patterns result, typically leading to accumulation of cellular material and thrombus formation. Typically, the wall of the vessel also progressively dilates and weakens, causing the aneurysmal sac to grow and often resulting in vessel rupture. Vessel rupture, in turn, often causes dramatic negative health consequences such as a stroke, when a cerebral vessel ruptures, or even death, when an abdominal aortic aneurysm ("AAA") ruptures. In light of these consequences, improved treatment methods and devices for aneurysms are constantly being sought. Although the following discussion focuses on AAA treatment, it is equally applicable to aneurysms in other locations.

The abdominal aorta is the portion of the aorta (the body's largest artery) located within the abdominal cavity. It functions to carry blood from the heart to the lower extremities and abdominal organs. Typically, the abdominal aorta has a diameter of about 2 cm to 2.5 cm in an adult and extends in a relatively straight path from the heart towards the groin, bifurcating into the iliac arteries to supply blood to the legs.

Generally, AAA's are located within the aorta between the renal arteries superiorly and in the bifurcation into the iliac arteries inferiorly. Although at first an aneurysm may be quite small, as the disease process continues an aneurysm enlarges, the aorta wall thins, and rupture typically results. When the aneurysm is less than 4.5 cm in diameter, danger of rupture is quite low. Even before the aneurysm grows large enough to pose a danger of rupture, however, it may cause other problems. The enlarged region often develops a thrombus that fills the distension so that blood flows only down the central region. Pieces of clot may break off from the thrombus and be carried away, resulting in blockages in the legs, lungs or even the brain.

Furthermore, an aneurysm typically enlarges at a rate of 0.3-0.5 cm per year. An aneurysm of 8 cm in diameter has approximately a 75% per year rupture risk, with consequences of rupture often being fatal. About 15,000 people die each year in the United States from ruptured AAA's. Over 60% of people who suffer a ruptured AAA die before reaching a hospital. Those who survive long enough to undergo surgery typically face a 50% survival rate. Even if the aneurysm is discovered before rupture, surgical repair is difficult and risky although surgery is 95% successful.

Traditional AAA repair methods include open abdominal surgery, in which the AAA is accessed through the abdomen, the portion of the aorta containing the aneurysm is clamped off, the aorta is incised, clot is removed and the aorta is manually repaired with stents, graft material and/or other devices. Newer, endovascular repair techniques generally involve placing a device, including one or more stents and/or grafts across the aneurysm through the vasculature rather than via an open surgical procedure.

A stent is generally a hollow, cylindrical, expandable device used to prop open a blood vessel to preserve or restore it patency. Stents are usually made of metallic mesh-like material, which may be either self-expanding or manually expandable. Self-expanding stents have shape memory capabilities, so that they can be compressed into a smaller shape for positioning at an area of treatment and then allowed to expand to attach to the desired area. Expandable stents are typically positioned at a desired location and then expanded by an inflatable device, typically a balloon, to attach the stent in the desired location.

Another device commonly used in vascular repair is a vascular graft, typically made of a synthetic material such as polytetrafluoroethylene (PTFE). An advantage of these synthetic grafts is that they are extremely flexible and can be readily compressed to a very small size for endovascular insertion. Application of a graft alone, however, generally requires suturing of the graft to the wall of the aorta, which requires an open procedure.

Many currently available AAA devices combine one or more synthetic graft components with one or more stent components. The stent component generally anchors the device in a desired location and maintains the patency of the vessel, while the graft component prevents thrombus from entering through the mesh-like structure of the stent and reinforces the wall of the aorta. Typically, such a device is placed across a AAA, often through a large aortic thrombus, to act as a new blood vessel. For example, some devices include a stent component for placement above the aneurysm, near the renal arteries, a graft component to cross the aneurysm, and one or more additional stent components to anchor the device distal to the aneurysm.

One recurring problem in AAA repair with stent or stent-graft devices is stress placed on such devices by motion. One type of motion that effects a AAA repair device is bending motion by the patient. Currently available devices try to address such motion by either providing a stronger, stiffer stent-graft to minimize bending of the device or providing a more flexible device to minimize stresses on the device.

Another type of motion that stresses AAA stent-graft devices but which has been largely ignored in AAA stent-graft design is longitudinal movement, causing stretching and/or compression of a stent-graft. Such stretching and/or compression may occur in either of at least two ways—acute stretching or compression of the vasculature due to the patient's body motion and gradual stretching or compression of the vasculature as the aneurysm grows or shrinks due to the presence of the graft. This stretching or compression applies significant stresses to the proximal and distal seals of the graft, and can be one of the major causes of graft migration and leakage of the seals over time. It can also lead to structural failures of the stent-graft, such as separation of graft elements fracture in the body of the graft or the like.

Another frequent problem faced in AAA repair with stent-graft devices is leakage of blood around the outside of the device. Such leakage allows blood to circulate through the aneurysm, rather than through the device. This flow of blood outside the device causes the blood pressure within the aneurysm to increase and the size of the aneurysm to progressively grow, increasing the risk of rupture. One cause of such leakage is inadequate initial attachment of the device to the internal surface of the wall of the aorta proximal to the aneurysm. If attachment, or "anchoring" of the proximal portion of the device is inadequate, blood typically leaks between the device and the wall of the aorta, into the aneurysm.

Leakage of blood around a AAA stent-graft may also occur when such a device becomes loose after an initially adequate anchoring. In other words, even if a stent-graft is initially anchored sufficiently, the device may lose its tight fit after a period of use. A loosened stent-graft may slip distally, pushed by the flow of blood, which may further compromise the fit of the device within the aorta, causing further leakage. When such loosening, slippage and/or leakage occurs in currently available stent-graft devices, the devices must typically be replaced via an additional surgical procedure.

Generally, leakage around a AAA stent-graft is usually caused by one or more stresses on the device. Two types of stresses—bending and longitudinal—have been discussed above. A third type of stress on the seal of a AAA stent-graft is diametrical expansion and contraction of the blood vessel at the seal location over time, without matching expansion of the graft. This is caused both by cyclical variations in blood pressure, as well as gradual expansion or contraction of the blood vessel over time. A fourth stress is the hydrostatic pressure of blood against the graft. For the upper seal of the AAA graft system in the aorta, this pressure equals the cross-sectional area of the graft times the aortic blood pressure. For an aorta diameter of 26 mm, and a blood pressure cycling between 80 mmHg and 150 mmHg, this force equals 0.823 sq. in.*1.55 psi-2.90 psi, or 1.28-2.39 lbs. A similar estimate of the hydrostatic stress on an iliac seal of 14 mm diameter gives an estimate of 0.37-0.69 lbs.

When a graft such as a knitted Dacron graft is affixed to the inner surface of a human artery, the body's natural healing response causes ingrowth of endothelial tissue, scar tissue or pannus into the graft element. This healing response will typically create a hemostatic seal of the graft to the vessel wall over time, unless that healing response is disturbed by stresses or motion of the graft relative to the vessel wall. The tissue which forms this seal typically does not have significant structural strength, and the stent-graft may often be easily pulled loose or dissected from the vessel wall when due to one or more of the mechanical stresses described above.

Although efforts have been made to design a AAA stent-graft having a stronger graft-vessel wall connection, these attempts have met with limited success. Designing the graft to apply additional radial outward force against the vessel wall only gains a certain amount of longitudinal resistance to movement or migration. Building the graft with hooks or other anchors increases the risk of trauma to the vessel wall and the risk of fatigue failure of those anchoring elements. Evidently, strengthening fixation of the graft at the seal areas may be limited.

Therefore, it would be advantageous to have devices and methods to provide treatment of AAA with reduced leakage, slippage and breakage of the AAA stent-graft device. Ideally, devices would include adequate anchoring features to prevent both leakage and slippage of the device. There is also a need for a flexible device to allow for repeated bending, stretching and compression forces over time without breaking or significantly reducing the efficacy of the device. It would also be desirable for such devices to be adjustable once placed in a location in the aorta for treatment, so that devices which lose their fit within the aorta may be adjusted rather than replaced. At least some of these objectives will be met by the present invention.

BRIEF SUMMARY OF THE INVENTION

Generally, the present invention provides devices and methods for treating aneurysms. Although many types of aneurysms may be treated, such as cerebral, carotid and coronary aneurysms, the following discussion focuses on the treatment of abdominal aortic aneurysms ("AAA"). More specifically, stent-graft devices and methods for treating AAA include self-expanding and/or balloon-expandable stent components and one or more graft components coupled with the stent components. Using various combinations of self-expanding stent members, balloon-expandable stent members, graft members, and/or anchoring members enhances the anchoring abilities of a stent-graft device to prevent leakage around it, and may further allow the device to be adjusted after placement at a site for treatment. Some embodiments further include a skirt graft member for further prevention of leakage and/or device slippage.

In one aspect of the invention, a stent-graft device for treating an abdominal aortic aneurysm comprises at least one stent member comprising at least one of a self-expanding stent member and a balloon-expandable stent member, and at least one tubular graft member coupled with the at least one stent member, the tubular graft member having a proximal end and at least one distal end.

In some embodiments, the stent member includes at least one self-expanding stent member and at least one balloon-expandable stent member coupled with the self-expanding stent member. Optionally, the at least one self-expanding member and the at least one balloon-expandable member comprise a plurality of alternating members, every other alternating member comprising either a self-expanding material or a balloon-expandable material. The balloon-expandable material may, for example, be made of stainless steel and the self-expanding material may be made of nitinol, though any other suitable material(s) may be used. In some embodiments, the alternating members are coupled together with one or more pieces of adhesive. Optionally, this adhesive may further couple the alternating members with the tubular graft member. In some embodiments, the alternating members are coupled together via one of welding, soldering or tying, though any other method and/or means for coupling the members is contemplated. In some embodiments, the alternating members comprise a plurality of diamond-shaped members coupled together to form a cylindrical stent, though any other shapes and configurations are contemplated.

In some embodiments, the at least one tubular graft member comprises a main graft member toward the proximal end of the tubular graft member and at least one leg having a proximal end and a distal end, each leg member being coupled with the main graft member at its proximal end and extending toward the distal end of the tubular graft member. Optionally, the at least one leg member may comprise two leg members for coupling the distal end of the tubular graft member with two iliac arteries branching from the abdominal aorta. In some embodiments, the two leg members comprise two sinusoidal leg members. Optionally, the two sinusoidal leg members may be helically intertwined. Furthermore, in some embodiments, each of the two leg members is coupled with an iliac stent member at its distal end. Sometimes the iliac stent member comprises at least one of a self-expanding stent member and a balloon-expandable stent member. In various embodiments, each of the two leg members is removably couplable with the main graft member. Also in some embodiments, the main graft member may be coupled with at least one stent member at the proximal end of the tubular graft member, and each of the at least one leg members is coupled with at least one stent member at the distal end of the tubular graft member. Optionally, the device may also include a skirt graft member coupled with at least one of the main graft member and the stent member near the proximal end and extending toward the distal end.

Some embodiments of the device also include a suprarenal anchoring member coupled with the stent member for anchoring the stent-graft device at a location superior to renal arteries branching from the abdominal aorta. For example, in some embodiments the suprarenal anchoring member comprises at least one of a self-expanding stent member and a balloon expandable stent member. The suprarenal anchoring may be coupled with at least one of the self-expanding stent member and the balloon expandable stent member by any suitable means, such as but not limited to wire, ribbon, rods and/or bands of material. Some embodiments may further comprise an infrarenal anchoring member coupled with at least one of the stent member and the suprarenal anchoring member for further anchoring the stent-graft device at a location inferior to the renal arteries. In some cases, the infrarenal anchoring member comprises at least one of a self-expanding stent member and a balloon expandable stent member. Alternatively, the infrarenal anchoring member may be included in some embodiments without a suprarenal member.

Any other suitable components may be included with a stent-graft device. In one embodiment, for example, a stent-graft further includes at least one expandable balloon member coupled with the at least one balloon-expandable stent member for expanding the balloon-expandable stent member. As mentioned, other embodiments include at least one skirt graft member coupled with at least one of the stent member and the tubular graft member at or near the proximal end of the tubular graft member and extending toward the distal end.

In another aspect of the invention, a stent device for treating an aneurysm includes at least one self-expanding stent member and at least one balloon-expandable stent member coupled with the self-expanding stent member. As described above, the at least one self-expanding member and the at least one balloon-expandable member may comprise, in some embodiments, a plurality of alternating members, every other alternating member comprising either a self-expanding material or a balloon-expandable material. The aspects of such a stent have been described above. Such a stent device may further include one or more graft devices coupled (or removably couplable) with the stent member(s). Such a graft member may have any of the aspects and characteristics already described.

In another aspect, a stent-graft device for treating an abdominal aortic aneurysm comprises: a proximal stent member for coupling the stent device with the abdominal aorta proximal to the aneurysm; at least one distal stent member for coupling the stent device with a blood vessel distal to the aneurysm; and at least one graft member coupled with and extending between the proximal stent member and the at least one distal stent member, at least a portion of the graft member having a sinusoidal shape. In some embodiments, the at least one distal stent member comprises two iliac stent members for coupling the stent-graft device with two iliac arteries branching from the abdominal aorta. Furthermore, in some embodiments, the graft member may include a main graft member coupled with the proximal stent member; and two leg members, each leg member coupled with the main graft member and one of the two iliac stent members. Alternatively, the at least one graft member may include a main graft member coupled with the proximal stent member and two leg members, each leg member removably couplable with the main graft member and coupled with one of the two iliac stent members.

In some embodiments, the proximal stent member and/or the distal stent member comprises at least one self-expanding stent member and at least one balloon expandable stent member coupled with the self-expanding stent member. Some embodiments further include a suprarenal anchoring member coupled with the proximal stent member for anchoring the stent-graft device at a location superior to at least one renal artery branching from the aorta. The suprarenal anchoring member may comprise, in some embodiments, at least one of a self-expanding member and a balloon expandable member. Some embodiments may further comprise at least one skirt member coupled with the proximal stent member and extending distally.

In yet another aspect, a kit for treating an abdominal aortic aneurysm comprises: at least one stent-graft device for treating the aneurysm; at least one stent-graft positioning device positioning the at least one stent-graft device in the abdominal aorta to treat the aneurysm; and instructions for using the stent-graft device and the positioning device.

In another aspect, a method for treating an abdominal aortic aneurysm involves: positioning at least one stent-graft device in the abdominal aorta in a location for treating the aneurysm, the at least one stent-graft device having at least one self-expanding member and at least one balloon-expandable member coupled to the self-expanding member, and deploying the at least one stent-graft device to contact a portion of the abdominal aorta with at least a portion of the device.

In some embodiments, positioning the at least one stent-graft device comprises positioning a proximal stent member at a location within the aorta inferior renal arteries which branch from the aorta and superior to the aneurysm. Optionally, positioning the at least one stent-graft device may also include positioning at least one distal stent member at a location within at least one iliac artery of a patient. Positioning the at least one stent-graft device may further include positioning at least one suprarenal anchoring member coupled with the at least one proximal stent member at a location within the aorta superior to the renal arteries. In some embodiments, positioning the at least one stent-graft device comprises positioning the device over at least one of a guidewire and a guide catheter. Also in some embodiments, positioning the device comprises positioning at least one helical leg portion of the device over at least one of the guidewire and the guide catheter.

In some embodiments, deploying the at least one stent member comprises: releasing the stent member from a containment member to allow the at least one self-expanding member to expand; and expanding the at least one balloon-expandable member with an expandable balloon device. Some embodiments may further include positioning a suprarenal anchoring member coupled with the stent-graft at a location within an aorta superior the renal arteries and releasing the suprarenal anchoring member from a containment member to allow the suprarenal anchoring member to expand and contact the wall of the aorta. Additionally, some methods may include adjusting the stent-graft member by expanding the at least one balloon-expandable member with a balloon expansion device. Still other embodiments may include positioning a tubular graft member coupled with at least one of the self-expanding member and the balloon expandable member across at least part of the aneurysm. Some embodiments include such steps as expanding a balloon member within at least part of the aneurysm, positioning a skirt member coupled with the stent-graft device within at least a portion of aneurysm and the like. In some embodiments, the at least stent-graft device comprises a plurality of coupled members, each of the coupled members comprising either a balloon-expandable material or a self-expanding material.

DETAILED DESCRIPTION OF THE INVENTION

Generally, the present invention provides devices and methods for treating aneurysms. Although many types of aneurysms may be treated, such as cerebral, carotid and coronary aneurysms, the following discussion focuses on the treatment of abdominal aortic aneurysms ("AAA"). More specifically, stent-graft devices and methods for treating AAA include self-expanding and/or balloon-expandable stent components and one or more graft components coupled with the stent components. Using various combinations of self-expanding stent members, balloon-expandable stent members, graft members, and/or anchoring members enhances the anchoring abilities of a stent-graft device to prevent leakage around it, and may further allow the device to be adjusted after placement at a site for treatment. Some embodiments further include a skirt graft member for further prevention of leakage and/or device slippage.

Although the following description focuses on embodiments of devices and methods for AAA treatment, these or other embodiments may suitably be used for treatment of many other aneurysms, such as those of the cerebral arteries, coronary arteries, the heart and/or the like. Furthermore, the following description typically focuses on placement of one integrated device across a AAA, from a location proximal to an aneurysm to locations within the iliac arteries. It should be understood that multiple devices, combinations of devices and the like may alternatively be used and that other treatment locations are contemplated. For example, some devices may not extend into the iliac arteries. Therefore, any devices and/or methods including the use of one or more stents having self-expanding and balloon-expandable features are contemplated within the scope of the present invention. The description of specific embodiments below should not limit the scope of the present invention as set forth in the claims.

Figure 1:
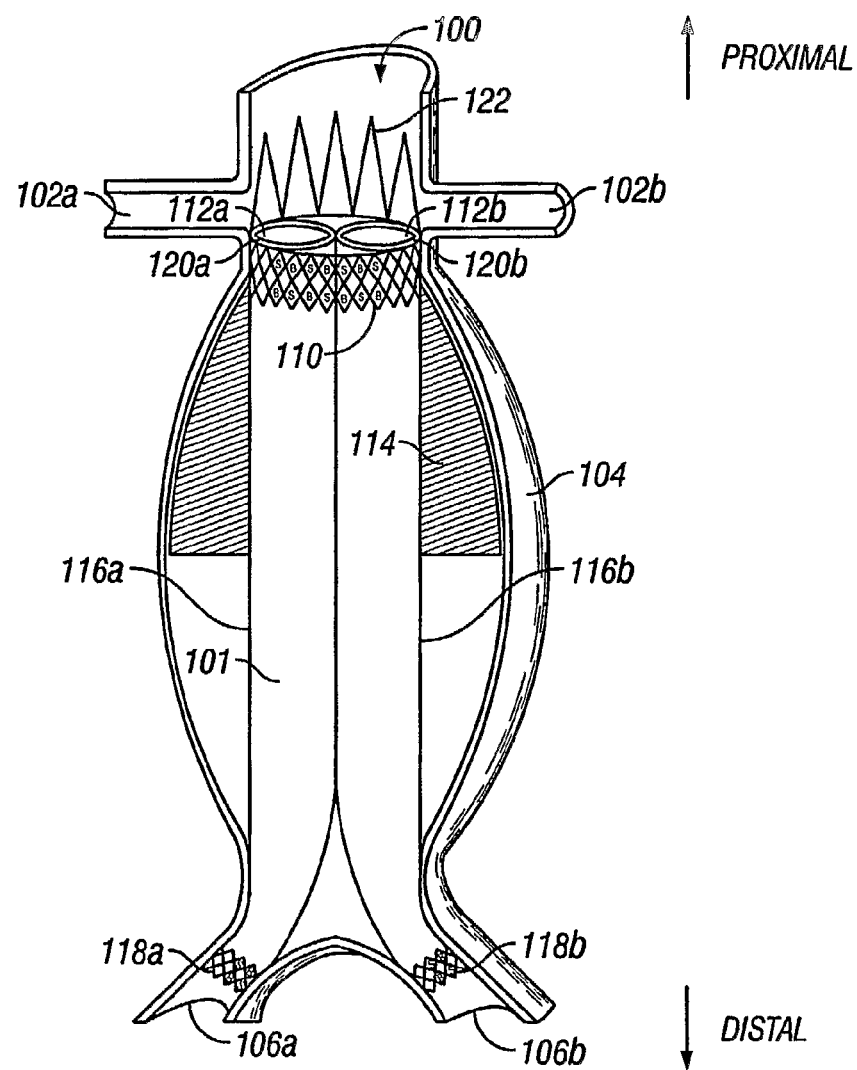
FIG. 1 is a perspective view of a stent-graft device in position for treating a AAA, according to one embodiment of the present invention.

That being said, and referring now to FIG. 1, an aorta 100 is shown with a right renal artery 102a, a left renal artery 102b, an aneurysm 104 in the wall of the aorta, a right iliac artery 106a and a left iliac artery 106b. One embodiment of a device 101 for treating aneurysm 104 suitably includes a first stent member 110, with a right tubular member 120a forming a right lumen 112a and a left tubular member 120b forming a left lumen 112b. The embodiment of device 101 in FIG. 1 also includes a second stent member 122 extending proximally from first stent member 110, two iliac legs 116a, 116b coupled with the two tubular members 120a, 120b, and two iliac anchoring stents 118a, 118b, each anchoring stent coupled with one of iliac legs 116a, 116b. Finally, some embodiments of device 101 will include one or more skirts 114 extending distally from first stent member 110 within aneurysm 104 for further positioning, holding in place and/or preventing leakage around device 101.

First stent member 110 and iliac anchoring stents 118a, 118b are pictured generally as a mesh material configured as a grid of diamond-shaped elements. In one embodiment, alternating diamond-shaped elements in a mesh may be formed from self-expanding and balloon-expandable materials. In FIG. 1, this pattern is designated by the labels in some of the diamonds of "S" for "self-expanding" and "B" for "balloon-expandable." As is described further below, such a configuration is only one possible embodiment and many other suitable embodiments for stents and stent components are contemplated.

It should be emphasized that FIG. 1 describes only one exemplary embodiment and that many different embodiments of devices for treatment of AAA are contemplated within the scope of the invention. For example, some embodiments may include only stents, some embodiments do not include second stent member 122, some embodiments do not include separate tubular members 120a, 120b and/or the like. Other embodiments may include more or fewer stent members, graft members, skirts and/or any other suitable configuration of elements for treating a AAA. In some embodiments, iliac legs 116a and 116b may be fully supported by stent or other scaffold structures along their entire length or over additional portions of their lengths between the terminal stents 110, 118a, and 118b. Also, as previously discussed above, this and other embodiments may be used or adapted for use in blood vessels other than the abdominal aorta, such as the carotid arteries, coronary arteries, cerebral vessels, and/or the like.

That being said, first stent 110 is generally configured to anchor device 101 by attaching to the wall of aorta 100 at a location between aneurysm 104 and renal arteries 102a, 102b. First stent 110 may thus include any device or combination of devices suitable for anchoring the overall device to a vessel wall. For example, in various embodiments first stent 110 may be entirely self-expanding, entirely balloon expandable or a combination of self-expanding and balloon expandable.

In one embodiment, as mentioned above and shown in FIG. 1, alternating sections of first stent 110 are made of nitinol, a self-expanding material (S), and stainless steel, a balloon-expandable material (B). For example, alternating diamond-shaped sections of first stent 110 are made from self-expanding and balloon-expandable materials. Such a combination may provide for a conveniently self-expanding stent which could be further expanded by a balloon, to attach securely to the wall of the aorta and prevent leakage of blood around the device. Many other materials and configurations for making a stent are commonly know to those skilled in the art and any suitable combination of materials, configurations, sizes and the like may be used to make first stent member 110. For example, the material used to manufacture stent member 110 may be formed in any suitable pattern or configuration. Alternatively, separate expansible stent sections or scaffolds may be laminated to each other such that the overall stent will have a combination of deformable and elastic characteristics. The different layers may be laminated along their entire interface surface, or otherwise held together at different discrete points about their common circumferential interface.

Tubular member 120 is attached to stent 110 and is then joined at the center to form separate tubular members 120a and 120b to form two lumens 112a, 112b. Such lumens 112a, 112b typically provide for attachment to first stent member 110 of two iliac legs 116a, 116b, so that tubular members 120a, 120b may direct blood flow into the legs 116a, 116b. Materials used to make grafts, such as polytetrafluoroethylene (PTFE) and other polymers, are well known to those skilled in the art and any suitable material may be used for tubular member 120. In some embodiments other grafts may be attached to first stent member 110, such as a graft on the outside of the stent and the like.

Skirt 114 extends distally from first stent member 110 and typically is configured to be positioned in contact with the inner wall of aorta 100. In various embodiments, skirt 114 may be made of all stent material, all graft material, or a combination of stent and graft material. As pictured in FIG. 1, skirt 114 is a relatively freely-hanging graft material which may be placed in contact with the inner wall of aorta 100. In other embodiments, skirt 114 includes multiple stent-like legs and no graft material. Any suitable configuration is contemplated.

Second stent member 122 is generally any stent configuration capable of further anchoring the device by attaching to a location proximal to renal arteries 102a, 102b—i.e., in a suprarenal location. Typically, second stent member 122 will include only stent material, so that blood flow through the device to renal arteries 102a, 102b is not reduced. However, second stent members 122 including graft material or other suitable materials are contemplated. As with first stent member 110, any suitable material, such as nitinol, stainless steel, a combination thereof, or the like, may be used to make second stent member 122. The second stent member 122 may be formed integrally with the first stent member 110 or may be formed as a discrete scaffold component which is either attached or unattached to stent 110.

Figure 10:
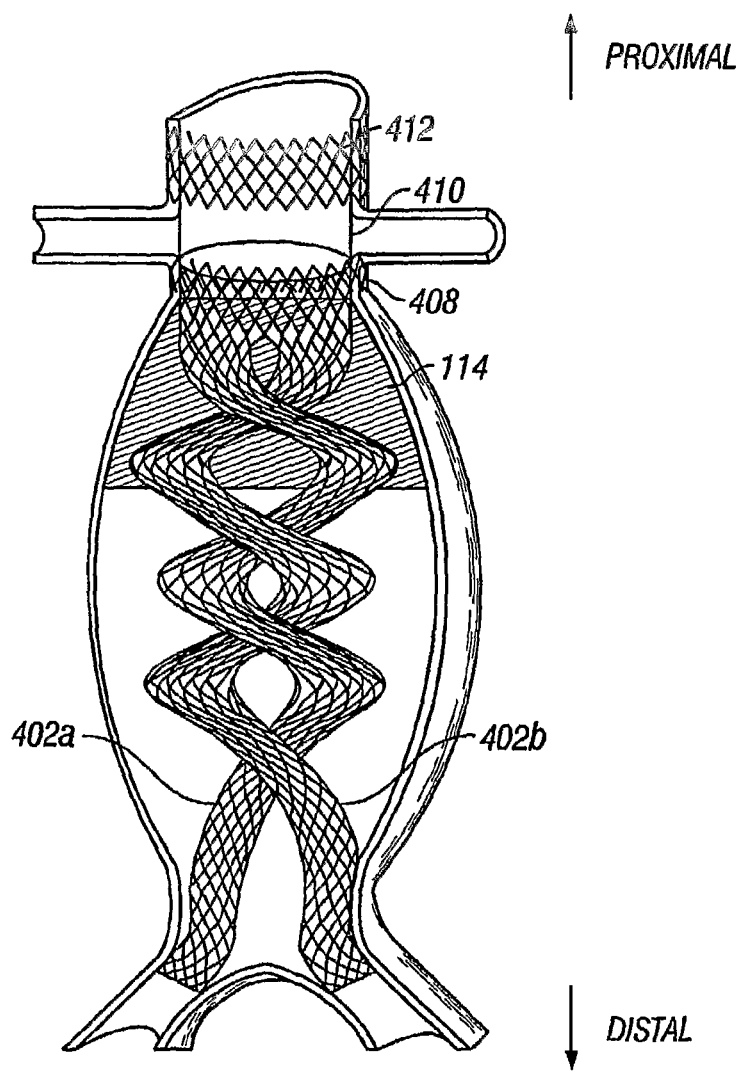
FIG. 10 is a frontal view of a stent-graft device having sinusoidal, helically wrapped leg portions and a suprarenal anchor in position for treating a AAA, according to another embodiment of the present invention.
Figure 11:
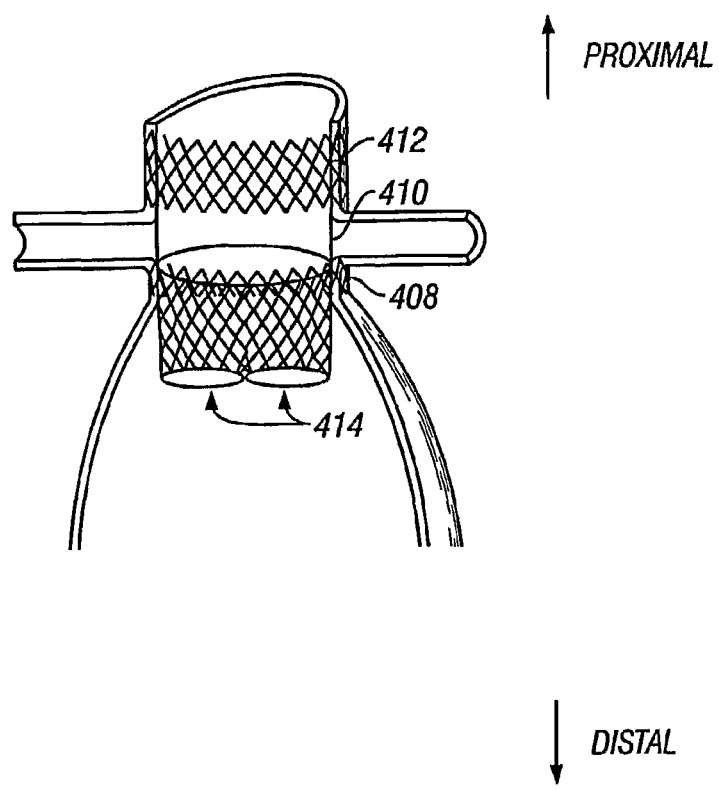
FIG. 11 is a frontal view of a portion of a stent-graft device having a suprarenal anchor in position for treating a AAA, according to another embodiment of the present invention.

With reference now to FIGS. 10 and 11, one embodiment of device 101 is shown, in which second stent member 122 comprises a suprarenal anchoring member 412. A proximal stent member 408 (which may variously be referred to as a "main stent member" or a "sealing stent member") is coupled with aorta 100 at an infrarenal location. Generally, suprarenal anchoring member 412 and proximal stent member 408 may be coupled by any suitable means. In various embodiments, for example, they may be coupled with a coupling member 410 such as wires, ribbons, cables, bands and/or the like. Such connections prevent foreshortening of the overall device during implantation. Although these figures do not show hooks or anchors which penetrate the aortic wall to enhance the fixation, such hooks could be included if desired. Also, as shown best in FIG. 11, in some embodiments proximal stent member 408 includes a two-lumen graft 414 into which two graft legs, as described further below, may be introduced. In other embodiments, however, proximal stent member 408 may have one leg pre-attached, both legs pre-attached or the like.

Iliac legs 116a, 116b may be a part of the device or may be provided separately from the device. Typically, iliac legs 116a, 116b will be positioned at the treatment area and attached to first stent member 110 after stent member 110 is in place. In some embodiments, however, iliac legs 116a, 116b may be pre-attached to first stent member 110 before insertion, may be attached to another component of the device, such as skirt 114, or the like. Generally, iliac legs 116a, 116b are anchored to iliac arteries 106a, 106b by iliac anchors 118a, 118b. Both legs 116a, 116b and anchors 118a, 118b may include any suitable combination of stent materials and/or graft materials, as previously discussed above in relation to first stent member 110. The legs 116a and 116b, as discussed above, are shown to be supported by stents only at their ends. Alternatively, the legs may be fully supported or additionally supported over the entire length or a portion thereof. Other supports are possible, including axial elements, discrete ring members attached to the legs, and the like.

Figure 2A:
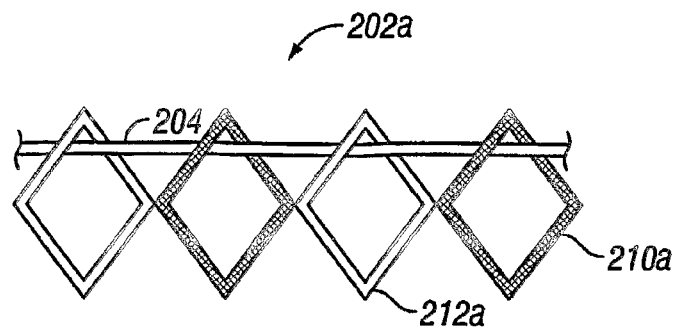
FIGS. 2a-c illustrate sections from a variety of stent devices, showing coupling of self-expanding and balloon-expandable members, according to various embodiments of the present invention.
Figure 2B:
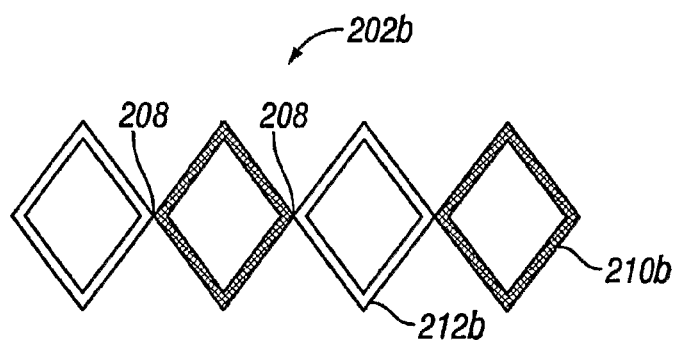
Figure 2C:
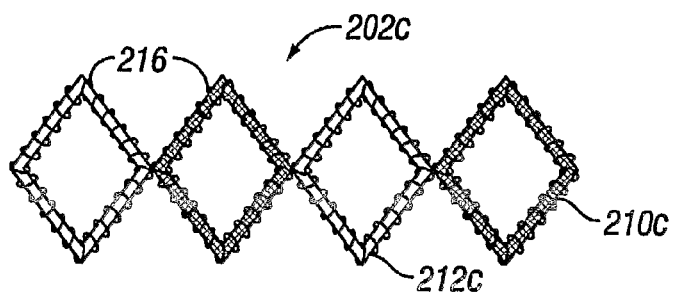

Referring now to FIGS. 2a-2c, sections 202a-c of various embodiments of stent members are shown. Sections 202a-c represent examples of stent members which may be used to form first stent 110, anchoring stent 122, second stents 118a, 118b and/or the like. As previously discussed, many other embodiments may be suitable and the devices of the present invention are not limited to diamond-shaped grids, meshes or the like.

In one embodiment, as shown in FIG. 2a, section 202a of stent members may include alternating balloon-expandable members 210a and self-expanding members 212a. Such members may be coupled together by any suitable means, for example a coupling device 204. Coupling device 204, in turn, may include any suitable device for joining stent members together. In one embodiment, coupling device 204 may comprise an adhesive tape. The tape may not only couple the stent members together, but may also couple the stent members to a graft material or other component of the device. Any suitable adhesive material may be used.

Referring now to FIG. 2b, in another embodiment balloon-expandable stent members 210b and self-expanding stent members 212b may be joined together at connection points 208 via welding, soldering, adhesive and/or any other suitable connection means. In some embodiments, for example, stent members may be joined by laser welding at connection points 208.

In yet another embodiment, with reference now to FIG. 2c, stent members 210c and 212c may be coupled via one or more wire connectors 216. Wire connectors 216 may be configured of metallic wire, suture material and/or any other suitable material for joining stent members. In some embodiments, wire connectors 216 are wound around stent members in a helical fashion. Wire connectors 216 may also be used in some embodiments to couple stent members to one or more graft members.

Generally, as described above, stent devices of the present invention may provide for prevention of leakage of blood around the stent, for improved positioning and placement of a AAA treatment device, for adjustment of a stent device after placement and/or the like. Providing a combination of self-expanding and balloon-expandable stent members within the same stent, such as in first stent 110, anchoring stent 112, iliac stents 118a, 118b, and/or other stents, allows a stent device to be partially self-deploying and partially manually expanded by a balloon or other expansive device. Methods of using devices of the present invention, therefore, typically involve both a self-expanding delivery component and a balloon-expandable delivery component.

Referring again to FIG. 1, inn one embodiment, a method according to the present invention includes delivering a device 101 at a location within an abdominal aorta for treatment of a AAA. Such delivery may be accomplished endovascularly or by any other suitable means. Typically, device 101 will be positioned to cross an aneurysm 104, from a location proximal to aneurysm 104 to a location distal to aneurysm 104. At the distal location, one or more portions of device 101 may be positioned for coupling with aorta 100, iliac arteries 106a, 106b, or both.

After device 101, or some portion of device 101, has been positioned in a desired location, one or more of the stents included in the device may be deployed. For example, first stent member 110 and anchoring stent member 122 may be deployed at a location proximal to aneurysm 104 before deploying the rest of device 101. Generally, a stent including self-expanding members may be deployed by releasing the stent from a sheath or other constraining device. If the stent also includes balloon-expandable members, it may be further expanded with a balloon device or other expansion device. For example, first stent member 110 may be positioned at a desired location within aorta 100, typically distal to renal arteries 102a, 102b and proximal to aneurysm 104, and then allowed to self-expand to contact the inner surface of the wall of aorta 100. First stent 110 may additionally be further expanded by positioning a balloon expansion device within the stent and expanding the balloon. This may allow first stent member 110 to achieve a firmer or more stable contact with aorta. Anchoring stent member 122, iliac stent members 118a, 118b, and/or any other stent members included in device 101 may be deployed in similar manner.

Figure 3:
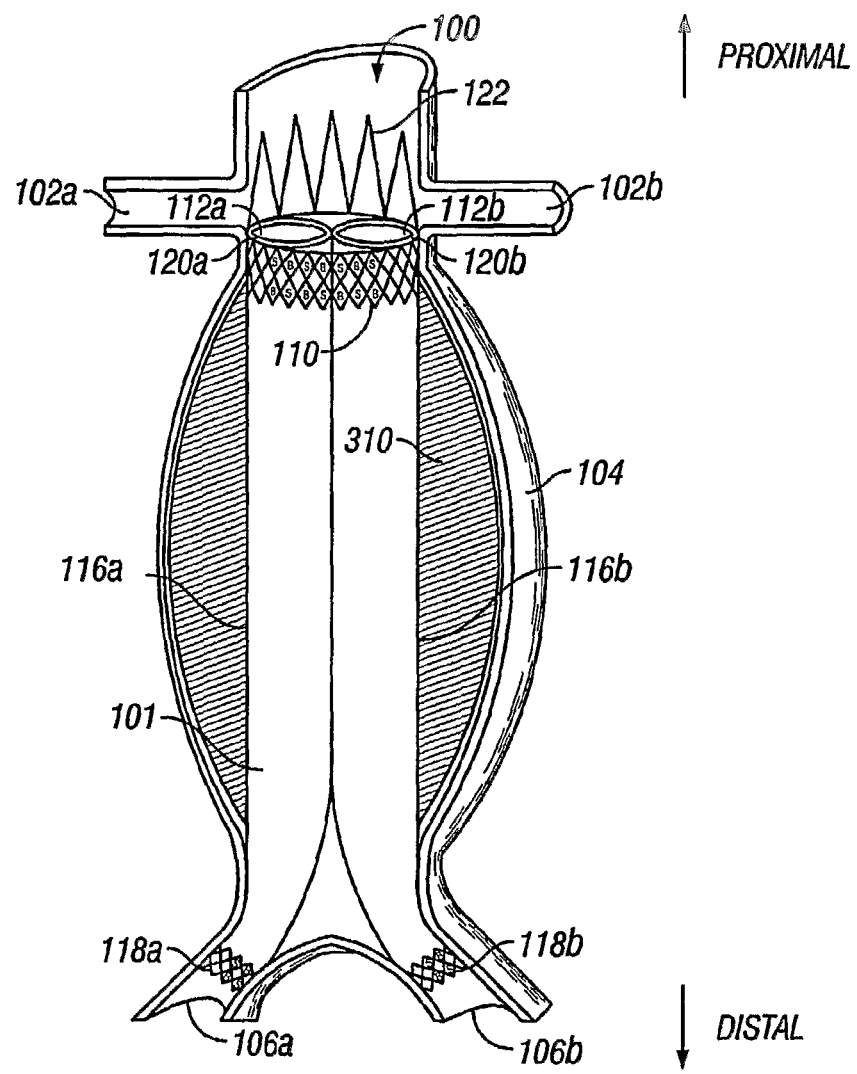
FIG. 3 is a perspective view of a stent-graft device in position for treating a AAA, according to another embodiment of the present invention.

Referring now to FIG. 3, another embodiment of device 101 suitably includes an inflatable balloon 310 or bladder. Balloon 310 may comprise graft material, stent material or a combination thereof, and may be attached to any portion of device 101 in any suitable manner. Balloon 310 will typically be inflatable with a liquid, air or other inflation means via an inflation lumen. When inflated, balloon 310 may assume any suitable shape for enhancing the fit of device 101 within aorta 100. For example, balloon 310 may expand to fill an aneurysmal sac 104 or any other irregularity in the shape of the inner wall of aorta 100. Generally, an inflated or expanded balloon 310 coupled with device 101 will be configured to help hold the device in a desired position within aorta 100 and to reduce movement or slippage of device 101 within aorta 100. As such, balloon 310 typically enhances leakage prevention.

Figure 4:
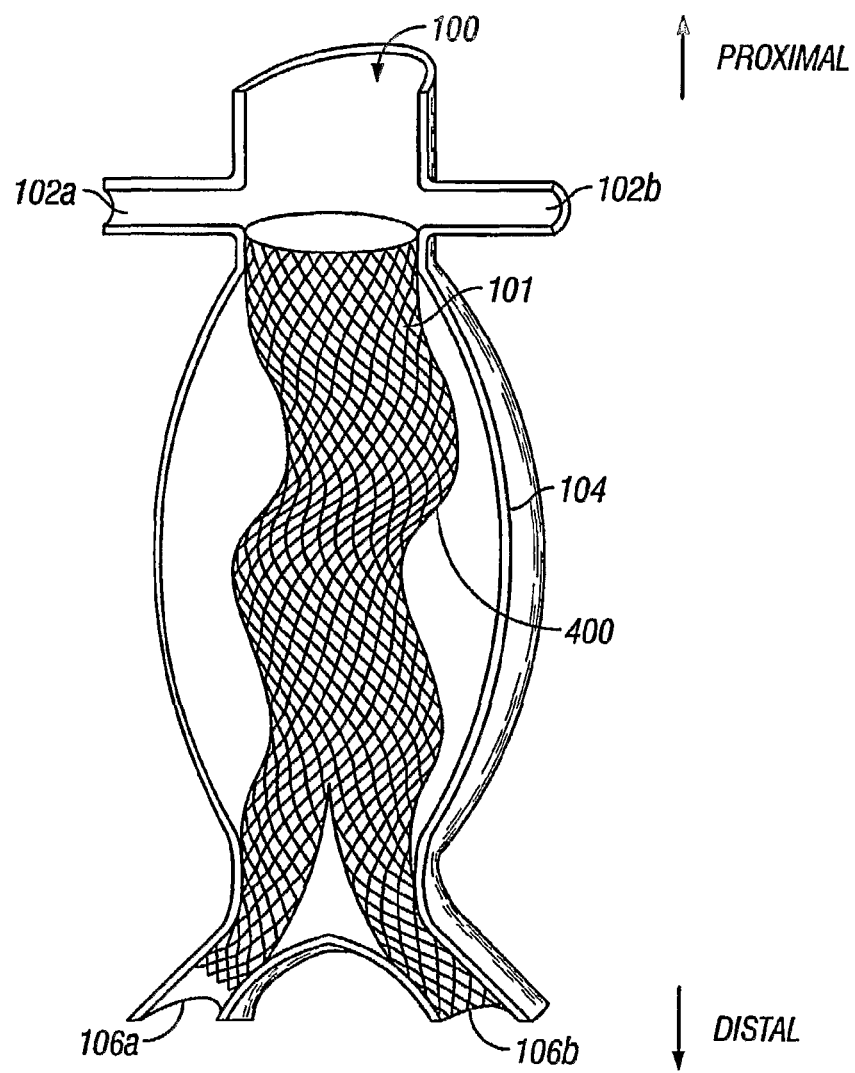
FIG. 4 is a frontal view of a stent-graft device having a sinusoidal portion in position for treating a AAA, according to another embodiment of the present invention.
Figure 5:
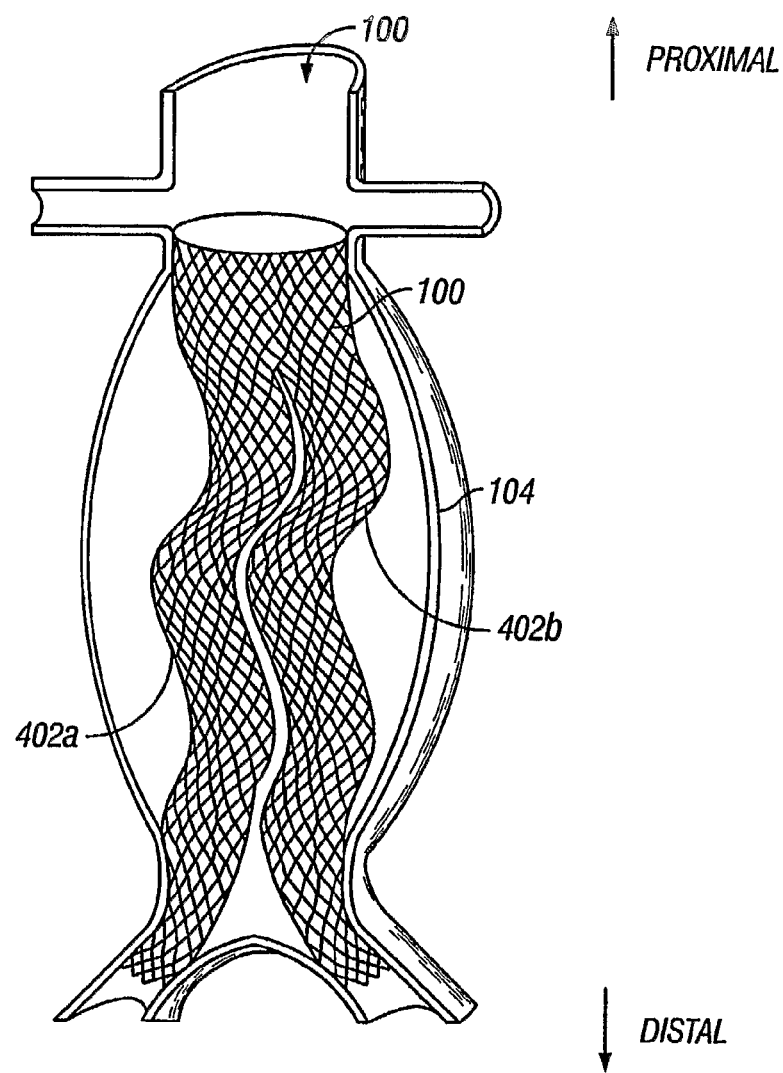
FIG. 5 is a frontal view of a stent-graft device having sinusoidal leg portions in position for treating a AAA, according to another embodiment of the present invention.

Referring now to FIG. 4, a frontal view of aorta 100 with aneurysm 104 shows an embodiment of device 101 having a sinusoidal-shaped graft portion 400. To enhance longitudinal flexibility (or "stretchiness" or "elasticity") of device 101, one or more bends may be included in a portion of device 101, such as sinusoidal graft portion 400. These bends allow device 101 to straighten and/or bend in one or more directions to absorb length changes to which device 101 is subjected and thus reduce stress/strain on device 101. FIG. 5 show a similar embodiment of device 101 having two sinusoidal graft legs 402a-b. In some embodiments, such devices 101 may be delivered in a straight configuration, for ease of delivery, and then may have shape memory characteristics allowing them to resume their sinusoidal shapes once delivered. Generally, sinusoidal graft portions 400 or legs 402 provide long-term elasticity and also provide relatively laminar flow, without causing dramatic atherosclerotic response within the graft due to turbulence or shear.

In other embodiments, which may look similar to those shown in FIGS. 4 and 5, graft legs might be made very flexible and be delivered with significant extra slack between the proximal and distal ends, so they form one or more bends in the body of the aneurysm. Such an arrangement would have almost zero column strength from the aortic fixation point to the iliac fixation point. Any relative flexion or tension between fixation points would put almost no stress on the graft or the fixation points. To ensure a desired amount of slack is introduced on deployment, the graft legs might be deployed first in the proximal anchor element, and then significant excess graft length might be deployed in the body of the aneurysm prior to deploying the other end of the graft in the iliac artery.

Figure 6:
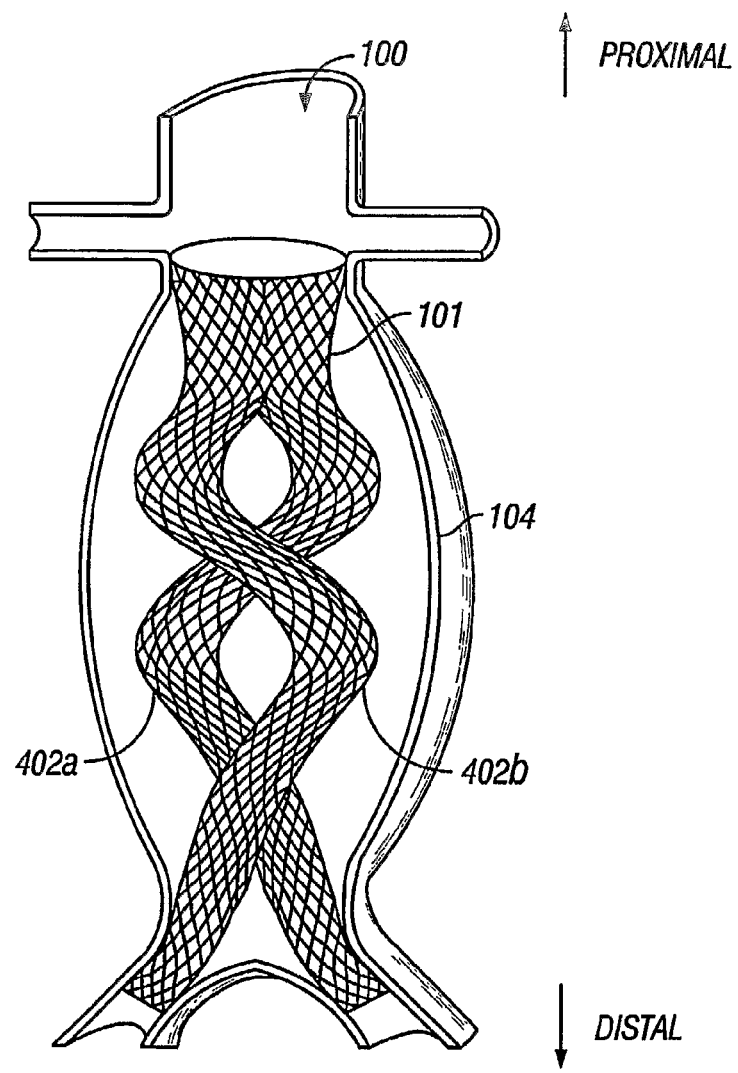
FIG. 6 is a frontal view of a stent-graft device having sinusoidal leg portions with extra length in position for treating a AAA, according to another embodiment of the present invention.
Figure 7:
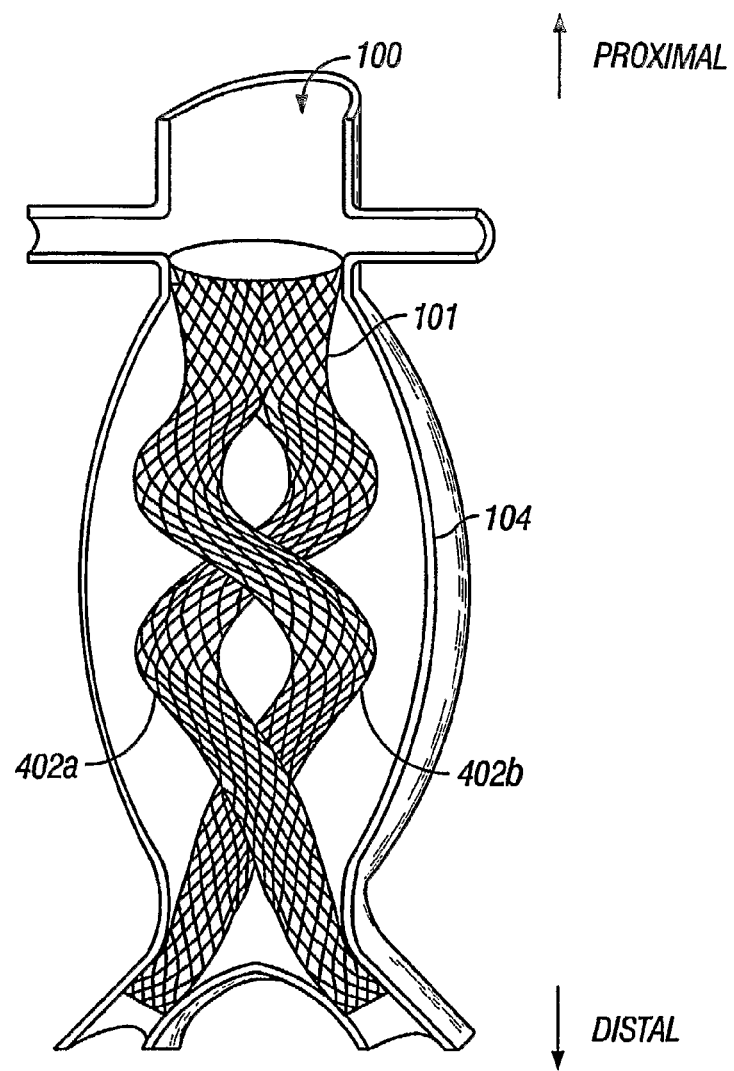
FIG. 7 is a frontal view of a stent-graft device having sinusoidal, helically wrapped leg portions in position for treating a AAA, according to another embodiment of the present invention.
Figure 8A:
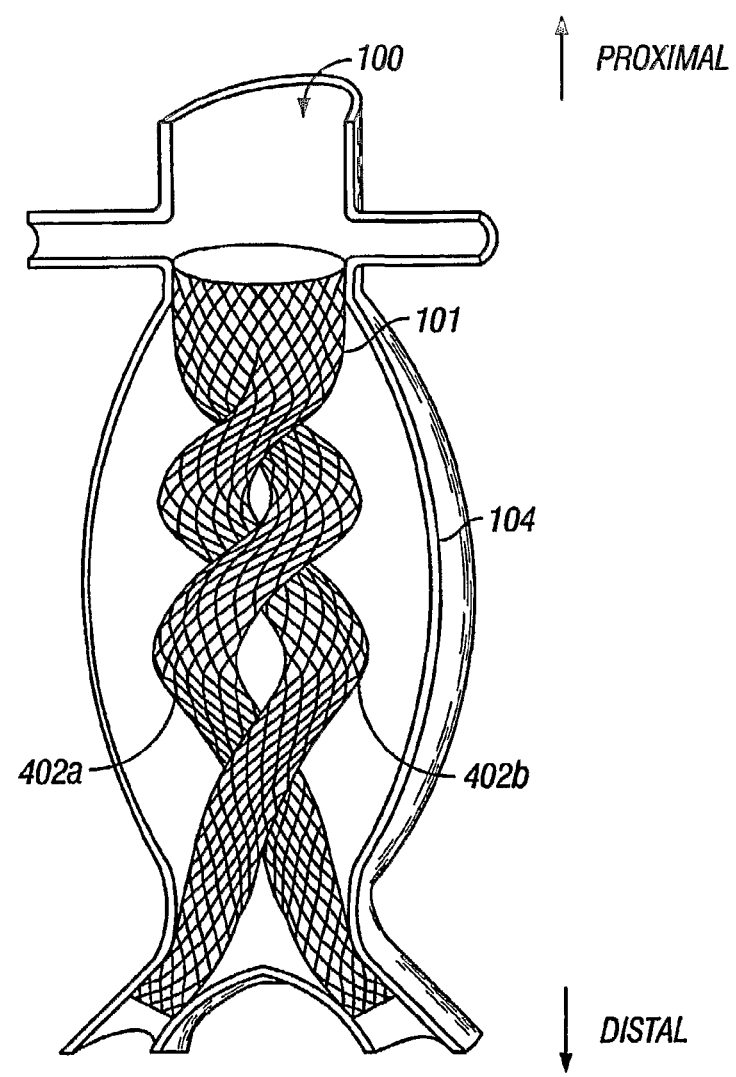
FIGS. 8A and 8B are frontal views of stent-graft devices having sinusoidal, helically wrapped leg portions in position for treating a AAA, according to various other embodiments of the present invention.
Figure 8B:
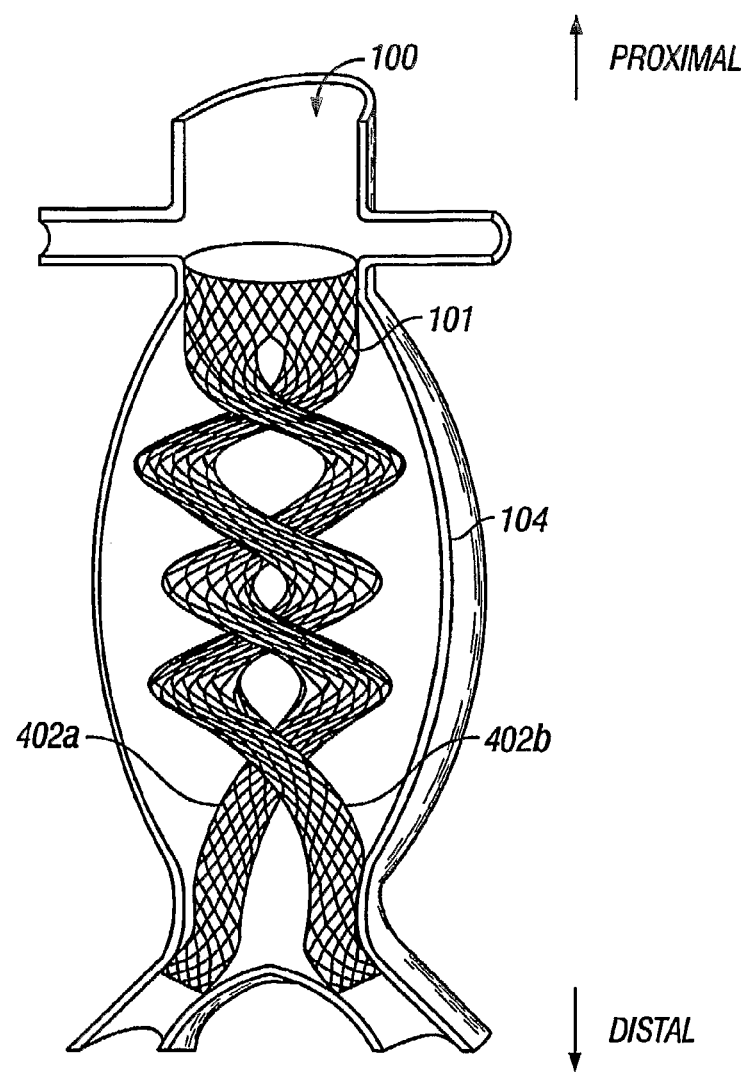

Referring now to FIGS. 6-8, in some embodiments, to prevent excessive acute bending of the excess graft in the aneurysm body, graft legs 402 may be wrapped around each other in a helical fashion. For example, graft legs 402 may be wrapped around each other to provide 360 degrees of helix, 540 degrees, or even more, as shown in the in FIGS. 8A and 8B, which show increasing amounts of helix. Furthermore, as shown in FIGS. 6 and 7, a helix of legs 402 may run in either direction. Generally, such helices may have any suitable configuration. Although graft legs 402 are typically loosely wrapped/entwined, to provide desired slack, any suitable wrapping pattern, tightness, and the like is contemplated within the scope of the invention.

Figure 9:
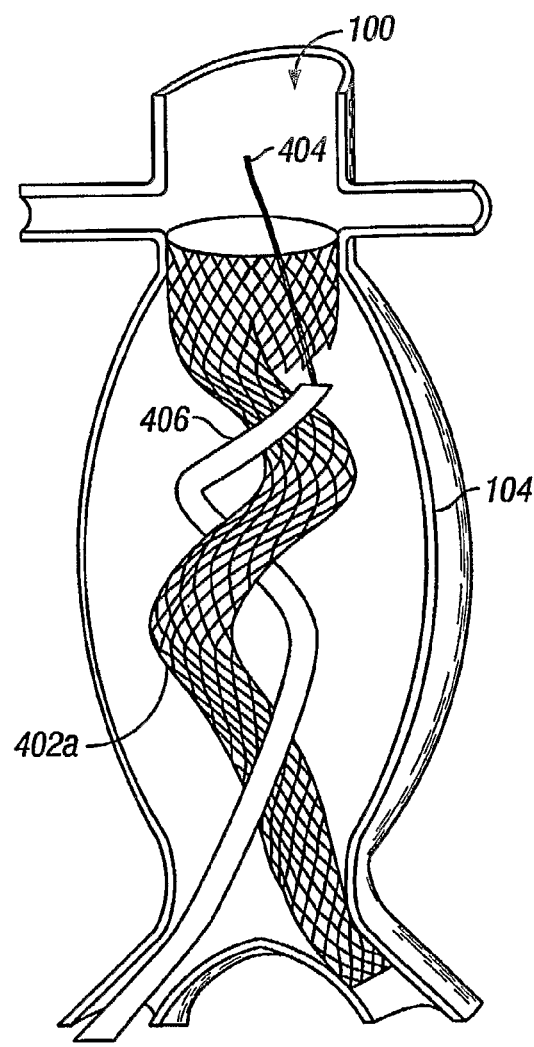
FIG. 9 is a frontal view of a stent-graft device having sinusoidal, helically wrapped leg portions and showing a guide catheter for in position for treating a AAA, according to another embodiment of the present invention.

Generally, the helical configuration just described and shown in FIGS. 6-8 will be deliverable by any suitable technique, such as delivery techniques already known in the art and/or novel methods. Referring now to FIG. 9, for example, in one embodiment the following delivery method may be used. First, one graft leg 402a is deployed with a reasonable amount of slack. This first-deployed leg 402a could either be integral with the upper graft element, or separate. Then, from the contralateral leg, a second leg 402b is introduced (not shown in FIG. 9). This second leg 402b would be introduced over a guidewire 404 and/or guiding catheter 406 which may have a pre-shaped helical curve at the distal end. Rotation of guidewire 404 and/or guiding catheter 406 would cause them to wrap around first graft leg 402a in the abdominal aorta 100, and they would then be advanced through the upper graft element. Second graft leg 402b would then be introduced over guidewire 404 and/or guide catheter 406 guide. In one embodiment there is an overlap of at least 2 cm and preferably 3 cm between legs 402 and the upper graft element, to minimize the risk of slippage and allow for some misalignment upon deployment by the physician, although other overlap sizes are contemplated.

In some embodiments, graft legs 402 will be preformed with the desired helical shape. The graft and delivery system would still be flexible, and would straighten out for introduction into the femoral or iliac artery, but would resume the appropriate helical shape once they were positioned within the body of aneurysm 104. This pre-shaped curve may facilitate delivery of a desired amount of slack and wrapping of one leg 402a around the other leg 402b during delivery. As already mentioned, and as shown in FIGS. 6 and 7, in some embodiments it may be advantageous to have a device 101 having a helix in one direction, while in others the opposite direction of helix may be superior. Any such configurations are contemplated within the scope of the invention.

As discussed, stent-graft devices of the invention may have any suitable configuration and may be made of any suitable material or combination of materials. In one embodiment, for example, device 101 may have a diameter in the range of about 12 mm to 16 mm, which may be compressible to a size acceptable for endovascular delivery, for example of 24 French or less, and more preferably less than 20 french, and even more preferably less than 14 french. In one embodiment, for example a Viabahn or Endobahn endovascular covered stent prosthesis manufactured by WL Gore may be used for one or more legs 402 of device 101, though any other suitable material(s) may be used.

Although exemplary embodiments of methods and devices have been disclosed herein, it should be apparent from the foregoing description that variations and modifications of such embodiments may be made without departing from the scope of the invention. Therefore, the above description should not be taken as limiting the scope of the invention which is defined by the appended claims.

What is claimed is:

1. A stent-graft device for treating an abdominal aortic aneurysm, the stent-graft device comprising:
    at least one stent member comprising at least one of a self-expanding stent member and a balloon-expandable stent member;
    at least one tubular graft member coupled with the at least one stent member, the tubular graft member having a proximal end and at least one distal end, said at least one tubular graft member, once deployed, comprising a main graft member toward the proximal end of the tubular graft member and at least one sinusoidal leg member toward the distal end of the tubular graft member relative to the main graft member, the at least one sinusoidal leg having a plurality of bends therealong such that one bend follows another bend axially along the sinusoidal leg, thereby forming a plurality of peaks and valleys axially therealong, each of said at least one sinusoidal leg member being coupled with the main graft member, said at least one sinusoidal leg member having shape memory biasing said at least one sinusoidal leg member toward a sinusoidal shape such that, once deployed, said at least one sinusoidal leg member is elongatable with elongation of the abdominal aortic aneurysm; and
    at least one skirt graft member coupled with at least one of the stent member and the tubular graft member at or near the proximal end of the tubular graft member and extending toward the distal end,
    wherein the skirt graft member is configured to be placed in contact with the inner wall of the aortic aneurysm when the stent-graft device is implanted adjacent to the abdominal aortic aneurysm.

2. A stent-graft device as in claim 1, wherein at least one stent member comprises:
    at least one self-expanding stent member; and
    at least one balloon expandable stent member coupled with the at least one self-expanding stent member.

3. A stent-graft device as in claim 2, wherein the at least one self-expanding member and the at least one balloon-expandable member comprise a plurality of alternating members, every other alternating member comprising either a self-expanding material or a balloon-expandable material.

4. A stent-graft device as in claim 3, wherein the balloon-expandable material comprises stainless steel and the self-expanding material comprises nitinol.

5. A stent-graft device as in claim 3, wherein the alternating members are coupled together with one or more pieces of adhesive.

6. A stent-graft device as in claim 3, wherein the adhesive further couples the alternating members with the tubular graft member.

7. A stent-graft device as in claim 3, wherein the alternating members are coupled together via one of welding, soldering or tying.

8. A stent-graft device as in claim 3, wherein the alternating members comprise a plurality of diamond-shaped members coupled together to form a cylindrical stent.

9. A stent-graft device as in claim 1, wherein the at least one sinusoidal leg member comprises two leg members for coupling the distal end of the tubular graft member with two iliac arteries branching from the abdominal aorta.

10. A stent-graft device as in claim 9, wherein said at least one sinusoidal leg member comprises two sinusoidal leg members.

11. A stent-graft device as in claim 10, wherein the two sinusoidal leg members are helically intertwined to provide at least 360 degrees of helix.

12. A stent-graft device as in claim 9, wherein each of the two leg members is coupled with an iliac stent member at its distal end.

13. A stent-graft device as in claim 12, wherein the iliac stent member comprises at least one of a self-expanding stent member and a balloon-expandable stent member.

14. A stent-graft device as in claim 9, wherein each of the two leg members is removably coupleable with the main graft member.

15. A stent-graft device as in claim 1, wherein the main graft member is coupled with at least one stent member at the proximal end of the tubular graft member, and each of the at least one leg members is coupled with at least one stent member at the distal end of the tubular graft member.

16. A stent-graft device as in claim 1, further comprising a suprarenal anchoring member coupled with the stent member for anchoring the stent-graft device at a location superior to renal arteries branching from the abdominal aorta.

17. A stent-graft device as in claim 16, wherein the suprarenal anchoring member comprises at least one of a self-expanding stent member and a balloon expandable stent member.

18. A stent-graft device as in claim 16, wherein the suprarenal anchoring is coupled with at least one of the self-expanding stent member and the balloon expandable stent member by at least one connective member selected from the group consisting of wire, ribbon, rods and bands of material.

19. A stent-graft device as in claim 16, further comprising an infrarenal anchoring member coupled with at least one of the stent member and the suprarenal anchoring member for further anchoring the stent-graft device at a location inferior to the renal arteries.

20. A stent-graft device as in claim 19, wherein the infrarenal anchoring member comprises at least one of a self-expanding stent member and a balloon expandable stent member.

21. A stent-graft device as in claim 1, further comprising:
    an infrarenal anchoring member for anchoring the stent-graft device at a location inferior to renal arteries branching from the abdominal aorta, the infrarenal anchoring member comprising at least one of a self-expanding member and a balloon-expandable member.

22. A stent-graft device as in claim 1, further comprising:
at least one expandable balloon member coupled with the at least one balloon-expandable stent member for expanding the balloon-expandable stent member.

23. A stent-graft device for treating an abdominal aortic aneurysm, the stent-graft device comprising:
a proximal stent member for coupling the stent device with the abdominal aorta proximal the aneurysm;
at least one distal stent member for coupling the stent device with a blood vessel distal to the aneurysm; and
at least one graft member coupled with and extending between the proximal stent member and the at least one distal stent member, at least a portion of the graft member being pre-shaped with a plurality of bends having shape memory such that, upon deployment, said at least a portion of the graft member is biased to have an elongatable sinusoidal shape and a sinusoidal outer surface having a plurality of peaks and valleys therealong such that a peak follows a valley axially along the sinusoidal graft member,
wherein the sinusoidal portion is configured to be positioned at least partly within the abdominal aortic aneurysm when the stent-graft device is implanted adjacent to the abdominal aortic aneurysm such that the stent graft device is elongatable with elongation of the abdominal aortic aneurysm.

24. A stent-graft device as in claim 23, wherein the at least one distal stent member comprises two iliac stent members for coupling the stent-graft device with two iliac arteries branching from the abdominal aorta.

25. A stent-graft device as in claim 24, wherein the at least one graft member comprises:
a main graft member coupled with the proximal stent member; and
two leg members, each leg member coupled with the main graft member and one of the two iliac stent members, wherein the two leg members are helically intertwined to provide at least 360 degrees of helix.

26. A stent-graft device as in claim 24, wherein the at least one graft member comprises:
a main graft member coupled with the proximal stent member; and
two leg members, each leg member removably coupleable with the main graft member and coupled with one of the two iliac stent members.

27. A stent-graft device as in claim 23, wherein at least one of the proximal stent member and the at least one distal stent member comprises:
at least one self-expanding stent member; and
at least one balloon expandable stent member coupled with the self-expanding stent member.

28. A stent-graft device as in claim 23, further comprising a suprarenal anchoring member coupled with the proximal stent member for anchoring the stent-graft device at a location superior to at least one renal artery branching from the aorta.

29. A stent-graft device as in claim 28, wherein the suprarenal anchoring member comprises at least one of a self-expanding member and a balloon expandable member being part of the same suprarenal anchoring member.

30. A stent-graft device as in claim 23, further comprising at least one skirt member coupled with the proximal stent member and extending distally.

31. A stent-graft device for treating an abdominal aortic aneurysm, the stent-graft device comprising:
at least one stent member comprising a plurality of expandable members coupled together circumferentially to form a cylinder, at least one of the expandable members that are coupled together circumferentially comprising a self-expanding material and at least another of the expandable members comprising a balloon-expandable material different from the self-expanding material, the self-expanding material and the balloon expandable material being part of the same at least one stent member; and
at least one tubular graft member coupled with the at least one stent member, the tubular graft member having a proximal end and at least one distal end, wherein the at least one stent member is configured to anchor the tubular graft member in an artery selected from the aorta and an iliac artery, and
wherein a portion of the at least one tubular graft member comprises a plurality of bends forming a sinusoidal shape with a plurality of peaks and valleys such that a peak follows a valley axially along the at least one tubular graft member.

32. A stent-graft device as in claim 31 wherein the at least one stent member has a first end portion, a second end portion, and a middle portion between the first end portion and second end portion, and wherein the plurality of expandable members are disposed in the middle portion.

33. A stent-graft device as in claim 32, wherein at least one of the first end portion and second end portion includes both self-expanding material and balloon-expandable material being part of the same end portion.

34. A stent-graft device as in claim 32, wherein the at least one stent member comprises balloon-expandable members and self-expanding members alternating in a pattern that is disposed in the middle portion, and wherein the pattern is arranged such that the middle portion is self-expanding to a first diameter and further balloon-expandable to a second diameter, the second diameter being larger than the first diameter.

35. A stent-graft device as in claim 31 wherein the balloon-expandable material alternates with the self-expanding material such that every other expandable member is balloon expandable and every other expandable member is self-expanding.

36. A stent-graft device as in claim 31 further comprising at least one skirt graft member coupled with at least one of the stent member and the tubular graft member at or near the proximal end of the tubular graft member and extending toward the distal end,
wherein the skirt graft member is configured to be placed in contact with the inner wall of the aortic aneurysm when the stent-graft device is implanted adjacent to the abdominal aortic aneurysm.

37. A stent-graft device as in claim 31, wherein the expandable members comprise diamond-shaped members.

38. A stent-graft device as in claim 31, wherein the stent member is configured to be self-expanding to a first diameter and further balloon-expandable to a second diameter, the second diameter being larger than the first diameter.

39. A stent-graft device for treating an abdominal aortic aneurysm, the stent-graft device comprising:
at least one stent member comprising a self-expanding stent layer and a balloon-expandable stent layer being part of the same at least one stent member, the self-expanding stent layer comprising a self-expanding material and the balloon expandable stent layer comprising a balloon expandable material different from the self-expanding material, the self-expanding stent layer and the balloon-expandable stent layer being laminated to one another radially from a central axis of the stent member; and at least one tubular graft member coupled with the at least one stent member, the tubular graft member having a proximal end and at least one distal end, wherein the at least one stent member is configured to anchor the tubular graft member in an artery selected from the aorta and an iliac artery, and wherein the at least one tubular graft member comprises a sinusoidal shape with a plurality of peaks and valleys therealong such that a peak follows a valley axially along the at least one tubular graft member.

40. A stent-graft device as in claim 39, further comprising at least one skirt graft member coupled with at least one of the stent member and the tubular graft member at or near the proximal end of the tubular graft member and extending toward the distal end, wherein the skirt graft member is configured to be placed in contact with the inner wall of the aortic aneurysm when the stent-graft device is implanted adjacent to the abdominal aortic aneurysm.

41. A stent-graft device as in claim 39, wherein the self-expanding stent layer and the balloon-expandable stent layer are laminated along an entire interface surface.

42. A stent-graft device as in claim 39, wherein the self-expanding stent layer and the balloon-expandable stent layer are held together at discrete points about a common circumferential interface.

43. A stent-graft device as in claim 39, wherein the self-expanding stent layer and the balloon-expandable stent layer are configured such that the stent member is self-expanding to a first diameter and further balloon-expandable to a second diameter, the second diameter being larger than the first diameter.

44. A stent-graft device as in claim 39, wherein the at least one tubular graft member comprises:

a main graft member toward the proximal end of the tubular graft member; and at least one leg having a proximal end and a distal end, each leg member being coupled with the main graft member at its proximal end and extending toward the distal end of the tubular graft member.

45. A stent-graft device as in claim 44, wherein the at least one leg member comprises two leg members for coupling the distal end of the tubular graft member with two iliac arteries branching from the abdominal aorta.

46. A stent-graft device as in claim 45, wherein the two leg members comprise two sinusoidal leg members having a plurality of bends and sinusoidal outer surfaces each having a plurality of peaks and valleys.

47. A stent-graft device as in claim 45, wherein the two leg members are helically intertwined to provide at least 360 degrees of helix.

* * * * *